United States Patent [19]

Neisen

[11] 4,204,931

[45] May 27, 1980

[54] PROCESS FOR THE PRE-TREATMENT OF NON-FERROUS METALS TO BE ELECTROPHORETICALLY COVERED WITH CERAMIC MATERIALS

[75] Inventor: Jürgen Neisen, Harsewinkel, Fed. Rep. of Germany

[73] Assignee: Miele & Cie GmbH & Co., Gutersloh, Fed. Rep. of Germany

[21] Appl. No.: 884,867

[22] Filed: Mar. 9, 1978

[30] Foreign Application Priority Data

Mar. 9, 1977 [DE] Fed. Rep. of Germany ....... 2710122

[51] Int. Cl.$^2$ ...................... C25D 13/02; C25D 13/20
[52] U.S. Cl. .............................. 204/181 N; 204/38 A; 204/38 C
[58] Field of Search ............. 204/181 N, 181 T, 38 C, 204/38 A

[56] References Cited

U.S. PATENT DOCUMENTS 3,935,088   1/1976   Kaup et al. ...................... 204/181 N
4,064,311  12/1977   McLean et al. ................... 204/38 C

*Primary Examiner*—Howard S. Williams
*Attorney, Agent, or Firm*—Allison C. Collard; Thomas M. Galgano

[57] ABSTRACT

Process for the pre-treatment of non-ferrous metals or alloys serving as foundation parts for dentures and the like to be covered electrophoretically with ceramic material, which comprises plating the foundation parts with zinc by electrolysis before carrying out the ceramic layer formation, the zinc plating being of a thickness to allow the entire metallic zinc to become oxidized by the oxygen generated by electrolysis occurring simultaneously with the electrophoretic layer formation of ceramic material, the zinc oxide forming a bridge to secure the ceramic cover layers to adhere to the non-ferrous metal parts.

2 Claims, No Drawings

PROCESS FOR THE PRE-TREATMENT OF NON-FERROUS METALS TO BE ELECTROPHORETICALLY COVERED WITH CERAMIC MATERIALS

The invention relates to a process for pre-treating of parts consisting of non-ferrous metals for application of enamel or the like ceramic materials thereon, making parts as they are conventionally used for dentures or similar articles.

It is generally known to form layers of enamel or another ceramic material on non-ferrous metals by spraying or brushing thereon a viscous muddy mass (a suspension of a ceramic mass) or by dusting of powdered enamel onto a heated work-piece. However, it is a disadvantage of the process that the length of time necessary for applying the ceramic layer is very considerable and that the application has to be repeated, sometimes several times, because defective spots are present.

Furthermore, the thickness of the applied layer of enamel is very uneven. Such an uneven thickness, particularly of the first or priming layer applied to the foundation of dentures, is quite harmful. This first ceramic layer practically serves as an adhesive bridge between the foundation material consisting of a non-ferrous metal or an alloy thereof, and the ceramic layers from which e.g. the surface of the tooth is shaped.

In making dentures, normally four ceramic layers are used for shaping the tooth and a cover layer coats the first ceramic basic layer. Since in all, six ceramic layers are used to cover the metallic foundation, the first or priming ceramic layer has to meet high requirements. It renders matters yet more difficult that the mechanical stress on these parts in later use is also quite high. If the first ceramic base layer is not formed evenly and without gaps, the necessary ceramic layers for shaping the tooth and the top layer will not adhere faultlessly and the costs for additional work at a later date will be excessively high. Since every one of the ceramic layers as well as their top layers have to be burned-in before the next layer is applied, the operating expenses are very high as well. In the conventional method of applying a ceramic base layer on the foundation body of a denture, the burning-in occurs after the ceramic layer has been applied. To obtain an even and gap-free basic ceramic layer is, in that case, to a high degree dependent on the manual skill of the operator.

It is the object of the invention to avoid these known shortcomings and to disclose a process for pre-treating non-ferrous metals and their alloys for an electrophoretic application of enamel or a like ceramic material thereon, wherein the application (layer formation) occurs evenly, rapidly and without defects, without requiring particular manual skills. The steps necessary for carrying out this process are more fully explained hereinbelow.

From the following description, several examples of carrying out the invention are apparent.

EXAMPLE (a)

Applying layers of a ceramic material on parts of dentures made of non-ferrous metals.

The metallic foundation bodies of parts of dentures or the like are de-greased and/or sandblasted. When the foundation body consists of a work-piece which is less noble than copper in the electromotive series, the metallic body may be subsequently activated in a cold, hydrochloric copper sulfate solution. Such activation is necessary, e.g., with bodies of cobalt-chromium alloys. With alloys of noble metals having a high gold content, the activation is not necessary.

Then the metallic body is zinc-plated electrolytically. The time of zinc-plating and therewith the thickness of the zinc layer depends on the following time of layer formation, of the ceramic material which is carried out electrophoretically. During the desired electrophoretic process, an unavoidable electrolysis takes place, in which the water present is partly decomposed into hydrogen and oxygen. The nascent oxygen forms at the work-piece. If the work-piece consists of a non-ferrous metal (nickel, chromium, platinum, palladium or a gold alloy) without intermediate zinc layer, the nascent oxygen is not, or only partly, capable of oxidizing the noble work-piece surface. Therefore the oxygen obtained is deposited on the work-piece in gaseous form. The ceramic layer is loosened or damaged thereby.

However, if a thin zinc layer is present on the surface of the work piece, there will not be any formation of gaseous oxygen on the surface of the work-piece during the electrolysis occurring simultaneously with the electrophoretic layer formation of the ceramic material, but the relatively electrochemically less noble zinc layer is preferably oxidized by the generated oxygen. Consequently, gas reactions due to liberated oxygen can no longer occur and the electrophoretically deposited enamel layer will adhere strongly to the surface of the work-piece.

The intermediate zinc layer between work-piece surface and ceramic surface must be of the accurate thickness which causes the entire pure zinc to be converted into zinc oxide during the electrophoretic layer formation. If the zinc layer is of greater thickness, the entire metallic zinc will not be converted into zinc oxide during the electrophoretic layer formation so that the enamel layer will not adhere satisfactorily on the work-piece surface, since metallic zinc does not lend itself to adherence of the ceramic layer.

The preferred thickness of the metallic zinc layer is at most 1 $mg/cm^2$ with a deposition time of the ceramic layer of several seconds.

When the thickness of the zinc is properly adjusted to the electrophoretic deposition time, the ceramic layer will adhere to the work-piece surface so strongly that the work-piece can be sprayed with water before the ceramic layer is being burned-on. This allows loosely adhering ceramic mass to be rinsed off.

The so obtained ceramic foundation layers are of very even thickness, do not exhibit blisters or defective spots, and can be burned-on after having been dried.

The subsequent shaping of the tooth surface and the following cover coating may be done by hand in the conventional manner.

The time it takes to effect the ceramic foundation layer application decreases from about 30 minutes to a few seconds. The applied layers are of a considerably higher quality and their adherence is improved.

EXAMPLE (b)

Electrophoretic layer formation of copper-containing metallic parts.

When copper-containing metallic parts, such as positioning pins of brass, or the like, are to be electrophoretically treated for layer formation, the same difficulties are obtained as with noble metal alloys. These difficulties are overcome by an appropriately adjusted zinc-plating before the electrophoretic treatment is carried out.

I claim:

1. A process for coating a non-ferrous metal with a ceramic material for dental applications, comprising the steps of:

zinc plating by electrolysis a non-ferrous base material to produce a metallic zinc layer thereon; and electrophoretically applying to said plated base material an even layer of ceramic material, said electrophoretically applying step simultaneously causing said zinc layer to convert into zinc oxide by electrolysis, and said zinc layer being initially adjusted to a sufficient thickness such that the conversion time of the entire metallic zinc layer into zinc oxide coincides with the concurrent electrophoretic coating time, thereby avoiding, on the one hand, that during the electrophoretic coating with the ceramic material the entire metallic zinc will have not yet been converted into zinc oxide, and avoiding, on the other hand, that the conversion of metallic zinc into zinc oxide will have been completed before the electrophoretic coating has been terminated, said electrophoretically applying step lasting only a few seconds, and said thickness of said metallic zinc layer not exceeding 1 $mg/cm^2$.

2. The process according to claim 1, wherein foundation bodies consisting of a metallic substance which is less noble than copper in the electromotive series are reactivated in a hydrochloric copper sulfate solution before the electroplating with zinc is carried out.

* * * * *